United States Patent
Chen et al.

(10) Patent No.: US 9,381,017 B2
(45) Date of Patent: Jul. 5, 2016

(54) LINEAR SURGICAL STAPLER WITH ROTATABLE OPERATION BUTTON

(71) Applicant: Touchstone International Medical Science Co., Ltd., Jiangsu (CN)

(72) Inventors: Wangdong Chen, Jiangsu (CN); Kaifen Fu, Jiangsu (CN); Teng Shan, Jiangsu (CN)

(73) Assignee: Touchstone International Medical Science Co., Ltd., Jiangsu (CN)

( * ) Notice: Subject to any disclaimer, the term of this patent is extended or adjusted under 35 U.S.C. 154(b) by 460 days.

(21) Appl. No.: 14/058,001

(22) Filed: Oct. 18, 2013

(65) Prior Publication Data
US 2014/0103094 A1    Apr. 17, 2014

Related U.S. Application Data

(63) Continuation of application No. PCT/CN2012/073717, filed on Apr. 10, 2012.

(51) Int. Cl.
*A61B 17/072* (2006.01)
*A61B 17/00* (2006.01)
*A61B 17/29* (2006.01)

(52) U.S. Cl.
CPC ......... *A61B 17/072* (2013.01); *A61B 17/07207* (2013.01); *A61B 2017/0042* (2013.01); *A61B 2017/291* (2013.01); *A61B 2017/2923* (2013.01); *A61B 2017/2924* (2013.01)

(58) Field of Classification Search
CPC .................................................. A61B 17/072
USPC ................ 227/19, 176.1, 180.1, 175.1, 175.3
See application file for complete search history.

(56) References Cited

U.S. PATENT DOCUMENTS

| | | | |
|---|---|---|---|
| 5,129,570 A | 7/1992 | Schulze et al. | |
| 7,334,717 B2 * | 2/2008 | Rethy | A61B 17/07207 227/175.1 |
| 7,407,076 B2 * | 8/2008 | Racenet | A61B 17/072 227/175.1 |
| 7,407,078 B2 | 8/2008 | Shelton, IV et al. | |
| 7,896,214 B2 | 3/2011 | Farascioni | |

FOREIGN PATENT DOCUMENTS

| | | |
|---|---|---|
| CN | 101028205 A | 9/2007 |
| CN | 101683282 A | 3/2010 |
| CN | 20211311 U | 1/2012 |
| EP | 1 304 083 A2 | 4/2003 |
| WO | 02/056784 A2 | 7/2002 |

* cited by examiner

*Primary Examiner* — Nathaniel Chukwurah
(74) *Attorney, Agent, or Firm* — Seed IP Law Group PLLC (57) ABSTRACT

A linear surgical stapler includes upper and lower jaws, an anvil and a cartridge respectively mounted on opposite far ends of the upper and lower jaws, a handle portion, a slider, and a button base relatively fixed to the slider. The lower jaw therein includes a staple drive bar and a cutter pusher. The slider is mounted with the button base. Each lateral side of the button base is pivotally associated with an operation button which is rotatable between a first status where an operating surface of the operation button is perpendicular to an axis of the linear surgical stapler, and a second status where the operating surface of the operation button is parallel to the axis of the linear surgical stapler. Since the operation buttons can be simultaneously collapsed adjacent to the jaws, the profile of the whole instrument and the packaging costs can be reduced.

18 Claims, 11 Drawing Sheets

LINEAR SURGICAL STAPLER WITH ROTATABLE OPERATION BUTTON

This application claims the benefit of priority to Chinese Patent Application No. 201110099716.8 titled "LINEAR SURGICAL STAPLER", filed with the Chinese State Intellectual Property Office on Apr. 20, 2011, the entire disclosure of which is incorporated herein by reference.

TECHNICAL FIELD

The present disclosure relates to a medical stapling instrument, and more particularly to a linear surgical stapler, which belongs to the technical fields of medical instruments.

BACKGROUND OF THE RELATED ART

Linear surgical staples have been widely used in surgical operations for stapling wounds, and stapling and cutting interior tissues. U.S. Pat. No. 5,129,570 discloses a typical linear surgical stapler which is provided with double functions of stapling and cutting. That is to say, the linear surgical stapler is capable of stapling wounds and simultaneously cutting spilth tissues. Such linear surgical staples usually include a pair of upper and lower jaws, an anvil and a cartridge respectively mounted on opposite far ends of the upper and lower jaws, and a handle portion for closing the upper and lower jaws. The lower jaw therein includes a staple drive bar and a cutter pusher provided with a cutter mounted on a far end thereof, wherein the staple drive bar and the cutter pusher are simultaneously movable along an axis of the linear surgical stapler. Both one end of the staple drive bar and one end of the cutter pusher are associated to a slider. The linear surgical stapler further includes an operation button for sliding the slider, the staple drive bar and the cutter. The operation button is usually mounted at a left side or a right side of the upper and lower jaws, and the operation button is fixed relative to the slider. The surface of the cartridge defines a plurality of slots arranged along the axis of the linear surgical stapler. Each slot therein is provided with a staple pusher and a staple. The operation button drives movement of the slider which further drives the staple drive bar to push the staple pushers in turn, and then the staples are pushed to move towards the anvil corresponding to the tissues to be sutured, and ultimately the cutter is driven to cut off or notch the tissues between the cartridge and the anvil.

BRIEF SUMMARY

An embodiment of the present application provides a linear surgical stapler with a new operation button which can be simultaneously opened to extend outside of the jaws or can be simultaneously collapsed to close to the jaws.

In order to solve the above technical problems, it is provided according to an illustrated embodiment of the present application a linear surgical stapler which includes upper and lower jaws capable of mutually being closed or opened with each other, an anvil and a cartridge respectively mounted on opposite far ends of the upper and lower jaws, and a handle portion for closing the upper and lower jaws. A surface of the cartridge defines a plurality of slots arranged along an axis of the linear surgical stapler. Each slot therein is provided with a staple pusher and a stapler engaging with the staple pusher. The lower jaw therein includes a staple drive bar and a cutter pusher provided with a cutter mounted on a far end of the cutter pusher. The staple drive bar and the cutter pusher are simultaneously movable along the axis of the linear surgical stapler. The staple drive bar sequentially drives the staple pusher in the process of moving. Both one end of the staple drive bar and one end of the cutter pusher are associated to a slider. The slider is mounted with a button base which is fixed relative to the slider. Each lateral side of the button base is pivotally associated with an operation button which is rotatable between a first status where an operating surface of the operation button is perpendicular to the axis of the linear surgical stapler, and a second status where the operating surface of the operation button is parallel to the axis of the linear surgical stapler.

In an embodiment, the two operation buttons are symmetrical with each other and are rotatable between the first status where the operating surfaces of the operation buttons are simultaneously perpendicular to the axis of the linear surgical stapler, and the second status where the operating surfaces of the operation buttons are simultaneously parallel to the axis of the linear surgical stapler.

In an embodiment, the button base and the slider are either integral of one piece or separately made.

In an embodiment, the button base defines a pivot hole playing a pivotal role and the pivot hole is located outside of the upper and lower jaws.

In an embodiment, the button base includes a main body fixed to the slider and a shoulder portion extending beyond the button base. The shoulder portion defines a pivot hole. The operation button includes a pivot end and an operating portion. A pin is provided to extend through the pivot end and the pivot hole so that the operation button is pivotally mounted to the button base.

In an embodiment, two lateral sides of the button base are associated with a pair of symmetrical shoulder portions each of which is pivotally mounted with the operation button.

In an embodiment, a side surface of the button base includes a plane surface and an arced surface smoothly connected with each other. The operation button includes a front rotating-stop surface for mating with the plane surface and the arced surface.

In an embodiment, the lower jaw includes a pair of ribs formed on lateral sides thereof. The operation button includes a rear rotating-stop surface for mating with exterior surfaces of the ribs.

In an embodiment, a top surface of the button base includes a first recess and a second recess perpendicular to the first recess. The operation button includes a protrusion selectively mating with the first recess or the second recess.

It is also provided according to an illustrated embodiment of the present application a linear surgical stapler which includes upper and lower jaws capable of mutually being closed or opened with each other, an anvil and a cartridge respectively mounted on opposite far ends of the upper and lower jaws, and a handle portion for closing the upper and lower jaws. A surface of the cartridge defines a plurality of slots arranged along an axis of the linear surgical stapler. Each slot therein is provided with a staple pusher and a stapler engaging with the staple pusher. The lower jaw therein includes a staple drive bar and a cutter pusher provided with a cutter mounted on a far end of the cutter pusher. The staple drive bar and the cutter pusher are simultaneously movable along the axis of the linear surgical stapler. The staple drive bar sequentially drives the staple pusher in the process of moving. Both one end of the staple drive bar and one end of the cutter pusher are associated to a slider. The slider is mounted with a pair of operation buttons which are rotatable respect to the slider. The operation buttons are rotatable between a first status where operating surfaces of the operation buttons are simultaneously perpendicular to the axis of the linear surgical stapler, and a second status where the operating surfaces of the operation buttons are simultaneously parallel to the axis of the linear surgical stapler. When the operating surfaces of the operation buttons are perpendicular to the axis of the linear surgical stapler, operating portions of the operation buttons located far from pivot ends protrude beyond the upper and lower jaws.

In an embodiment, each operation button includes a driving gear pivotally mounted to the slider, and the slider includes even number of pinion gears for meshing with the driving gear.

In an embodiment, pivot portions of the operation button and the button base are of a piezoelectric material.

Beneficial effects of at least some embodiments include:

The operation buttons can be simultaneously opened to extend beyond the upper and lower jaws to meet particular surgery requirements.

The operation buttons can be simultaneously collapsed to close to the jaws so as to reduce the profile of the whole instrument and reduce the packaging and transportation costs.

After completing the surgery, the operation buttons is driven to move backwardly and be collapsed to realize indication of the surgery.

The operation button is fit for practical use because of its simple structure and easy assembly.

DETAILED DESCRIPTION OF THE PREFERRED EMBODIMENTS

Figure 1:
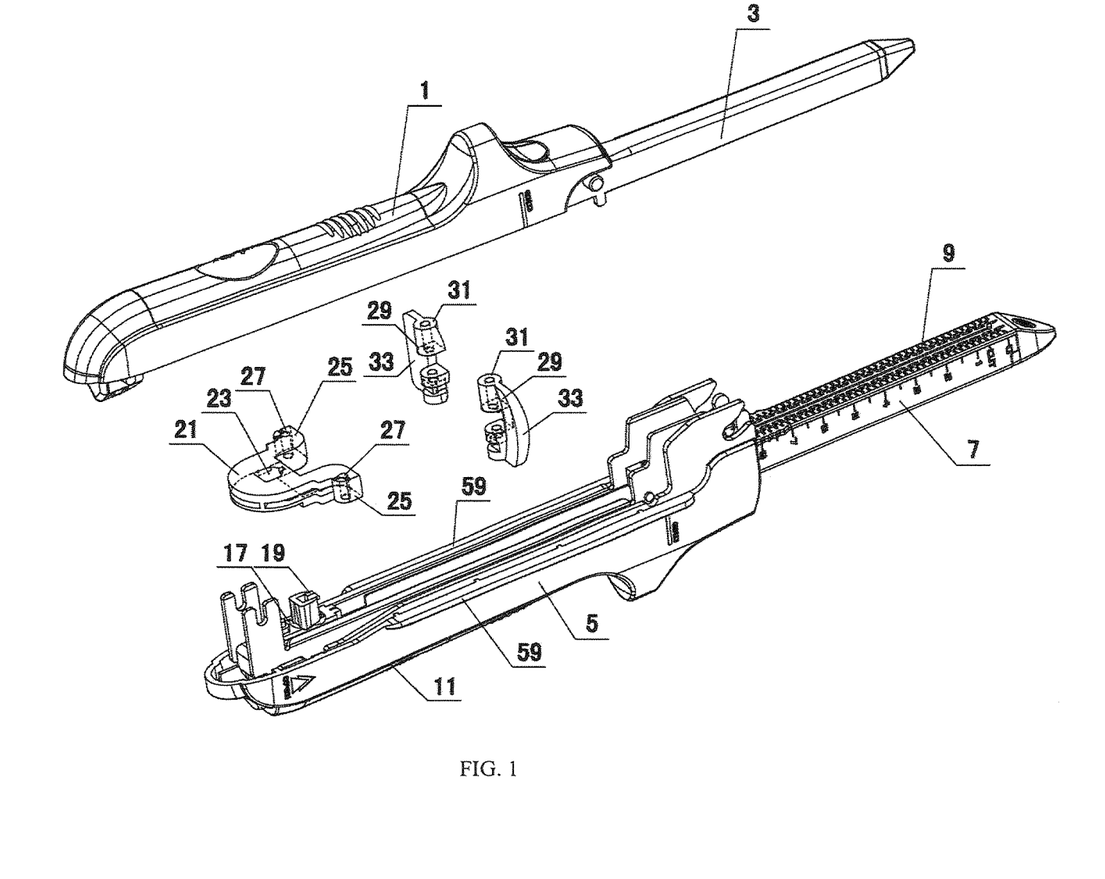
FIG. 1 is an exploded view of a linear surgical stapler in accordance with a first illustrated embodiment of the present application.
Figure 2:
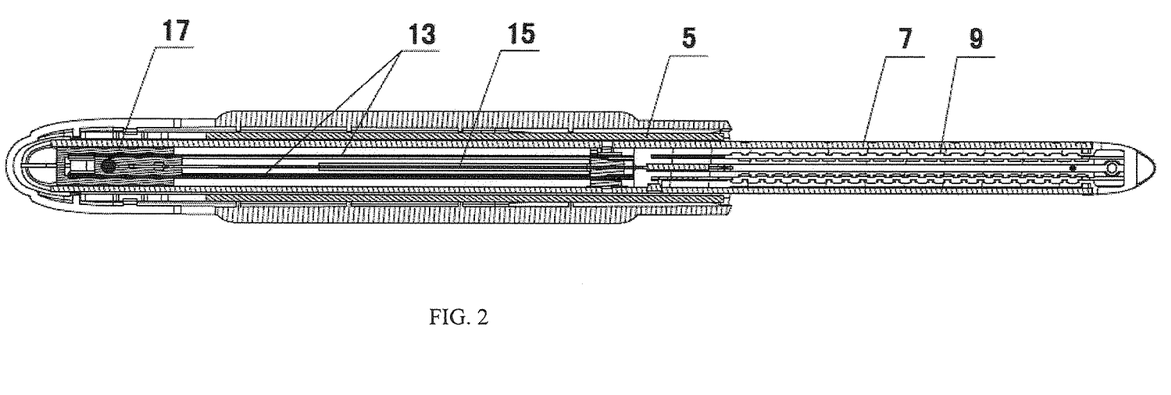
FIG. 2 is a cross-sectional view of the linear surgical stapler in accordance with the first illustrated embodiment of the present application.

Referring to FIGS. 1 and 2, the present application discloses a linear surgical stapler including upper and lower jaws 1, 5 capable of mutually being closed or opened with each other. The upper jaw 1 includes an anvil 3 located at a far end thereof. The lower jaw 5 includes a cartridge 7 located at a far end thereof. The lower jaw 5 is pivotally mounted with a handle portion 11 for closing the upper and lower jaws 1, 5.

The lower jaw 5 is U-shaped and includes a staple drive bar 13 slidable along an axis of the linear surgical stapler, and a cutter pusher 15 provided with a cutter on a far end of the cutter pusher 15 (as shown in FIG. 2). The cartridge 7 is received in the U-shaped lower jaw 5. A surface of the cartridge 7 defines a plurality of slots 9, generally in four rows, arranged along an axis of the linear surgical stapler. Each slot 9 therein is provided with a staple pusher and a stapler engaging with each other (consistent with the prior art, not shown). During movement of the staple drive bar 13, the staple-pushing jaws are sequentially driven by the staple drive bar 13 as a result that the staples are pushed outside of the slots 9 of the cartridge 7.

Figure 3:
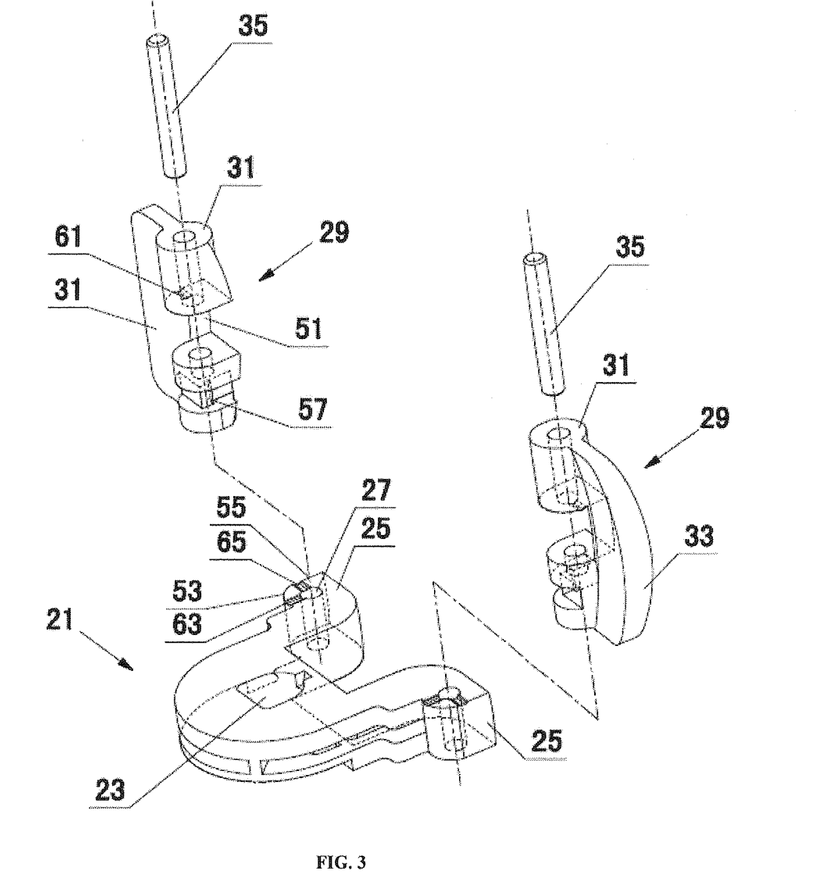
FIG. 3 is an enlarged view of a button base and an operation button as shown in FIG. 1.

Referring to FIGS. 1 to 3, according to a first embodiment, both one end of the staple drive bar 13 and one end of the cutter pusher 15 are associated to a slider 17. Movement of the slider 17 is capable of driving movement of the staple drive bar 13 and the cutter pusher 15.

The slider 17 is mounted with a button base 21 which is fixed relative to the slider 17 along the axis of the linear surgical stapler. According to the illustrated embodiment, the slider 17 includes a protrusion 19 and the button base 21 defines a mounting hole 23 to receive the protrusion 19, as a result that the button base 21 can be fixed to the slider 17. Certainly, the button base 21 and the slider 17 can be either separately manufactured, or integral of one piece which means that the two are completely fixed.

According to the first embodiment, each of the lateral sides of the button base 21 is pivotally mounted with an operation button 29. The two operation buttons 29 are symmetrically with each other. Referring to FIG. 3, the button base 21 includes a main body fixed to the slider 17 and a pair of symmetrical shoulder portions 25 protruding lateral sides of the button base 21. Each shoulder portion 25 includes a pivot hole 27. Each operation button 29 includes a pivot end 31 and an operating portion 33 connecting with the pivot end 31. Besides, a pin 35 is provided to extend through the pivot end 31 and the pivot hole 27 so that the operation button 29 is pivotally mounted to the button base 21. According to the first embodiment, the operating portion 33 includes a flat surface as an operating surface. The operator applies force to the operating surface so as to slide the operation button 29.

A side surface of the button base 21 includes a plane surface 55 and an arced surface 53 smoothly connected with each other. The operation button 29 includes a front rotating-stop surface 51 for mating with the plane surface 55 and the arced surface 53. The lower jaw 5 includes a pair of ribs 59 formed on lateral sides thereof. The operation button 29 further includes a rear rotating-stop surface 57 for mating with exterior surfaces of the ribs 59.

An embodiment of an operating process of the first embodiment will be described in detail in conjunction with accompanying drawings.

Figure 4:
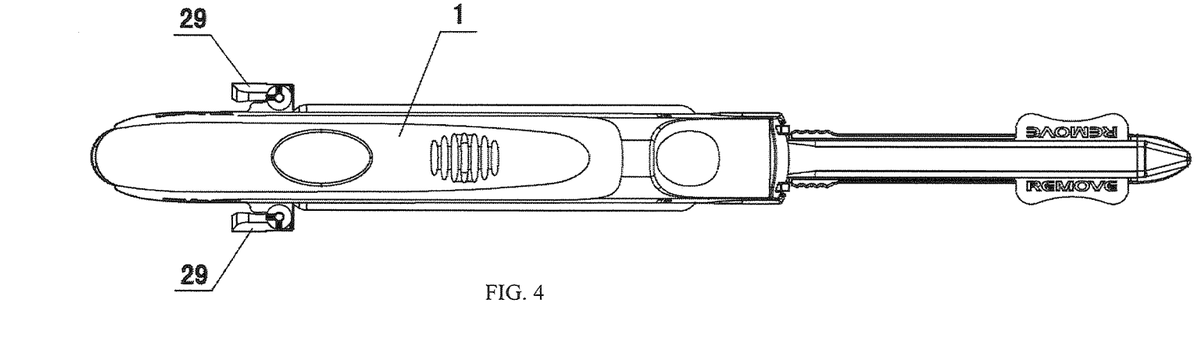
FIG. 4 is a top view of an initial status of the linear surgical stapler in accordance with the first illustrated embodiment, wherein an axis of the operation button is parallel to that of the linear surgical stapler.
Figure 5:
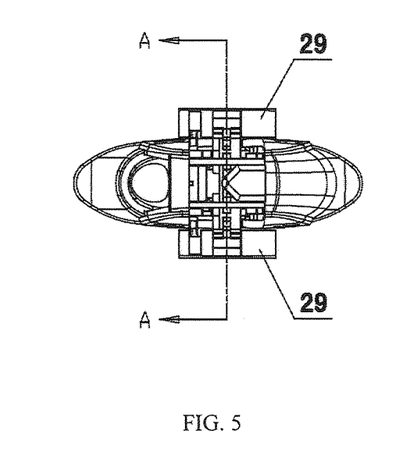
FIG. 5 is a left side view of FIG. 4.
Figure 6:
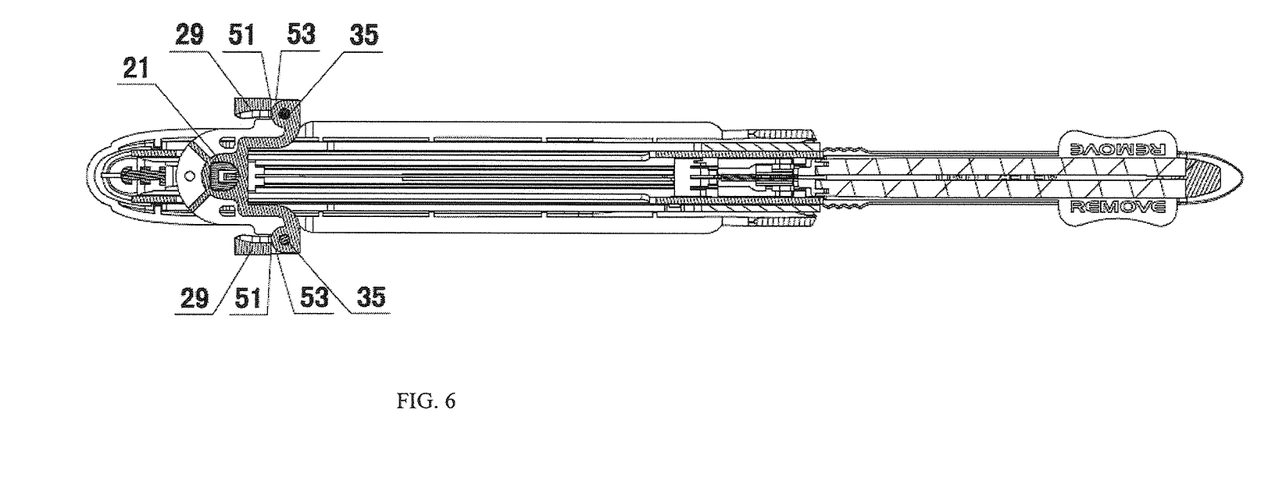
FIG. 6 is a cross-sectional view taken along line A-A of FIG. 5.

Referring to FIGS. 4 to 6, an initial status of the linear surgical stapler in accordance with the first embodiment is disclosed. Under this condition, the operating surfaces of the two operation buttons 29 are both parallel to the axis of the linear surgical stapler. In such initial status, since the operation buttons 29 are both collapsed to the upper and lower jaws 1, 5, the profile of the whole instrument is relatively small and the packaging can be produced relatively small, and thus reducing the raw materials and costs. Of course, even if the linear surgical stapler according to the first embodiment is provided with only one operation button 29, as long as the operation button 29 is collapsed, the profile of the whole instrument is also relatively small comparing with the prior arts. Besides, in such initial status, the front rotating-stop surface 51 is tangent to the arced surface 53 of the button base 21 so that the operation button 29 is rotatable about the pin 35.

Figure 7:
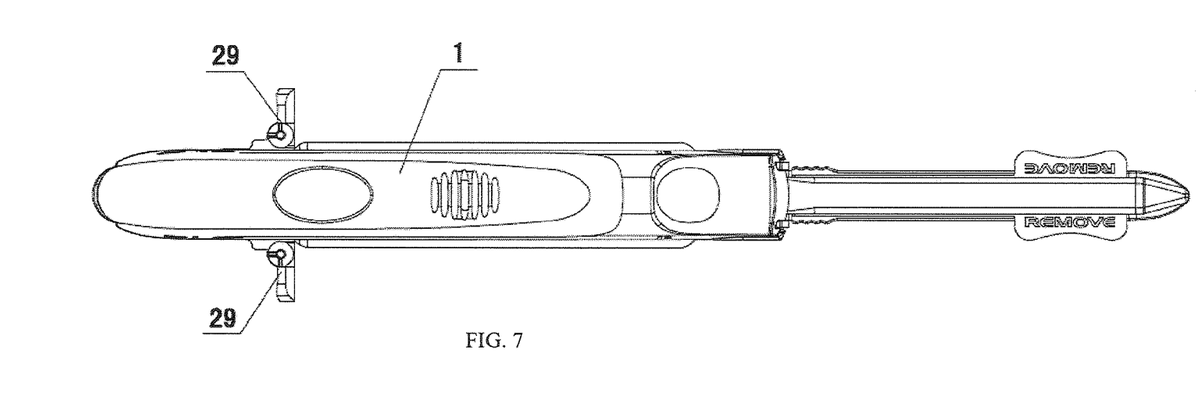
FIG. 7 is a top view of an operating status of the linear surgical stapler in accordance with the first illustrated embodiment, wherein the axis of the operation button is perpendicular to that of the linear surgical stapler.
Figure 8:
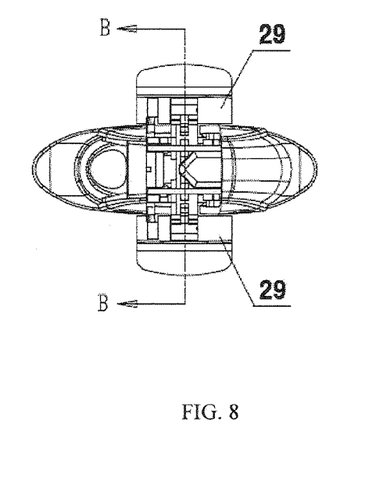
FIG. 8 is a left side view of FIG. 7.
Figure 9:
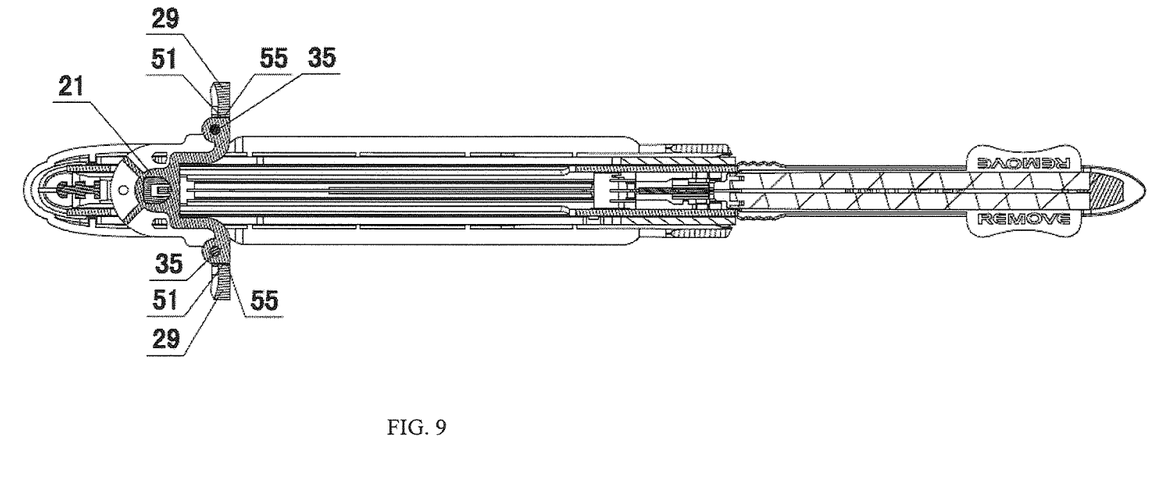
FIG. 9 is a cross-sectional view taken along line B-B of FIG. 8.

Referring to FIGS. 7 to 9, an operating status of the linear surgical stapler in accordance with the first embodiment is disclosed. Under this condition, the operating surfaces of the two operation buttons 29 are both substantially perpendicular to the axis of the linear surgical stapler. The operating portions 33 far from the pivot ends 31 protrude beyond the upper and lower jaws 1, 5, which means that the operation buttons 29 are in an opened position. In such operating status, since the front rotating-stop surface 51 engages with the plane surface 55 of the button base 21, the plane surface 55 is capable of preventing the operation buttons 29 from further rotating. As a result, when the operation buttons 29 move towards the far end of the linear surgical stapler, the reaction force of the plane surface 55 will cause the operation buttons 29 and the button base 21 relatively fixed, thereby the doctor can use both of his hands to drive the operation buttons 29 to complete special surgeries.

Referring to FIG. 3, since the operation buttons 29 rotate between two positions, a top surface of the button base 21 includes a first recess 63 and a second recess 65 perpendicular to each other, and each operation button 29 includes a protrusion 61 selectively mating with the first recess 63 or the second recess 65. As a result, when the protrusion 61 engages with the first recess 63, the operating surfaces of the operation buttons 29 are parallel to the axis of the linear surgical stapler, and the linear surgical stapler is in the initial status. When the protrusion 61 engages with the second recess 65, the operating surfaces of the operation buttons 29 are perpendicular to the axis of the linear surgical stapler, and the linear surgical stapler is in the operating status. Under this arrangement, the position of the operation buttons 29 can be further stabilized to avoid wobbling.

Figure 10:
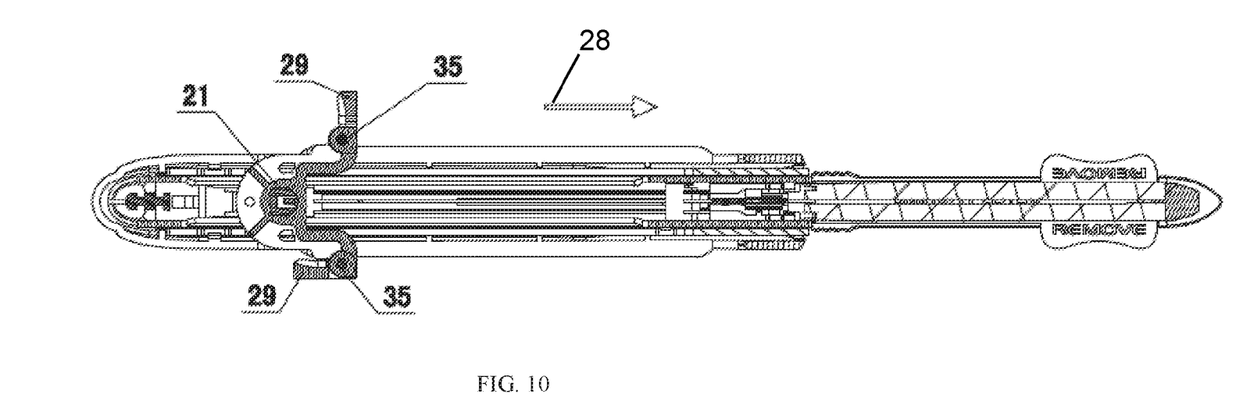
FIG. 10 is a cross-sectional view of an operating status of a linear surgical stapler in accordance with a second illustrated embodiment of the present application.
Figure 11:
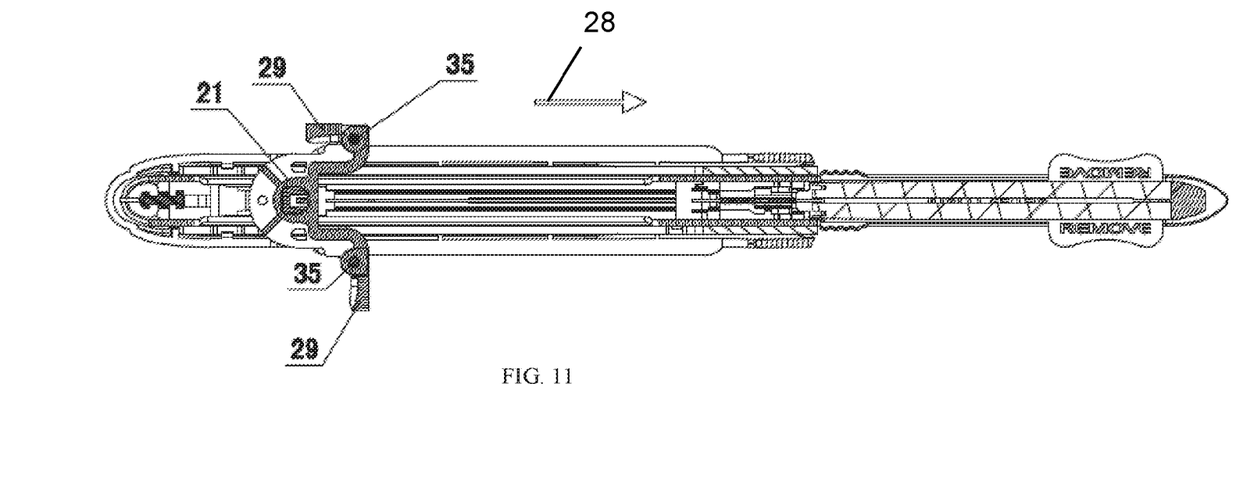
FIG. 11 is a cross-sectional view of an operating status of a linear surgical stapler in accordance with a third illustrated embodiment of the present application.

FIGS. 10 and 11 disclose schematic operating statuses of the linear surgical stapler in accordance with second and third embodiments, respectively. In the first embodiment, the buttons 29 are rotatable between a first status where the operating surfaces of the operation buttons 29 are simultaneously perpendicular to the axis of the linear surgical stapler, and a second status where the operating surfaces of the operation buttons 29 are simultaneously parallel to the axis of the linear surgical stapler. Different from the buttons 29 of the first embodiment, the two buttons 29 of the second and third embodiments are selectively rotatable between two statuses where the operating surface of one of the operation buttons 29 is perpendicular to the axis of the linear surgical stapler while the operating surface of the remaining operation buttons is parallel to the axis of the linear surgical stapler. For example, as shown in FIG. 10, in the second embodiment, only the left operation button 29 is under an operating status (in the direction of arrow 28). As shown in FIG. 11, in the third embodiment, only the right operation button 29 is under an operating status (in the direction of arrow 28).

In the above three embodiments, positions of the pivot holes 27 which play pivotal roles of the button base 21 are located outside of the upper and lower jaws 1, 5. The purpose of this arrangement is for easily assembling and simplifying the structure of the upper and lower jaws 1, 5.

Figure 12:
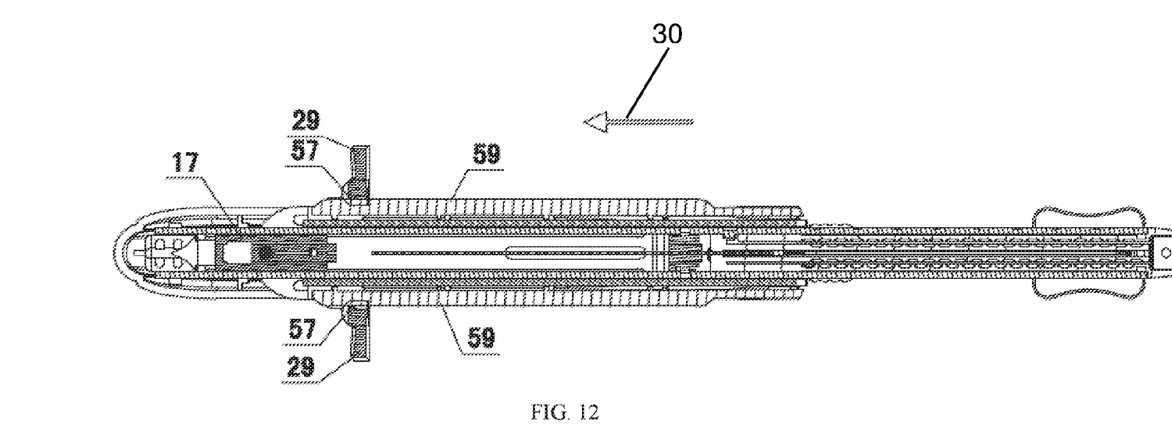
FIG. 12 is a cross-sectional view of the linear surgical stapler which begins to move rearwardly, in accordance with the first illustrated embodiment of the present application.
Figure 13:
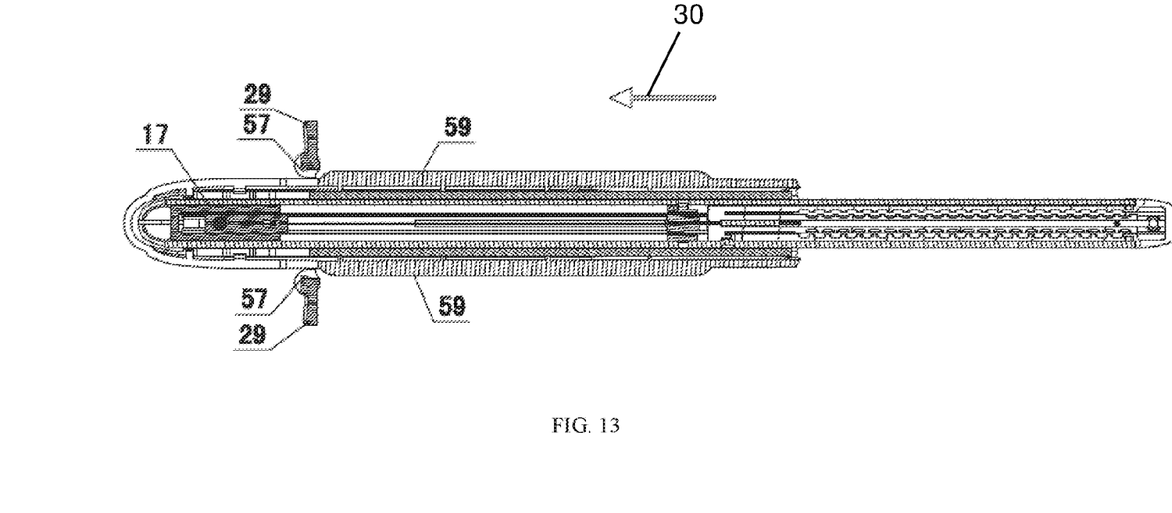
FIG. 13 is a cross-sectional view of the linear surgical stapler which finishes move rearwardly, in accordance with the first illustrated embodiment of the present application, wherein the operation button breaks away from ribs.

FIG. 12 discloses a cross-sectional view of the linear surgical stapler of the first illustrated embodiment after completing the surgery. The operation buttons 29 move rearwardly along the arrow 30 of FIGS. 12 and 13. Each rear rotating-stop surface 57 of the operation buttons 29 is a flat surface and engages with corresponding exterior surfaces of the ribs 59 which are located at the lateral sides of the lower jaw 5. With the flat surfaces engaging with each other, the rotation of the operation buttons 29 is restricted as a result that the operation buttons 29 will be able to retreat from the far end of the linear surgical stapler to a position disclosed in FIG. 13. Under this condition, the operation buttons 29 have completely retreated in position and the rear rotating-stop surface 57 disengages with the ribs 59. As a result, after the reaction force between the flat surfaces there between disappears, the operation buttons 29 is rotatable about the pin 35 back to the initial position as shown in FIG. 6. Besides, the operation buttons 29 also function as an instruction effect, i.e., when the operation buttons 29 can be rotated relative to the button base 21, it proves that the operation buttons 29 and the slider 17 have completely retreated in place, the suture is finished and the instrument is ready to be opened.

Figure 14:
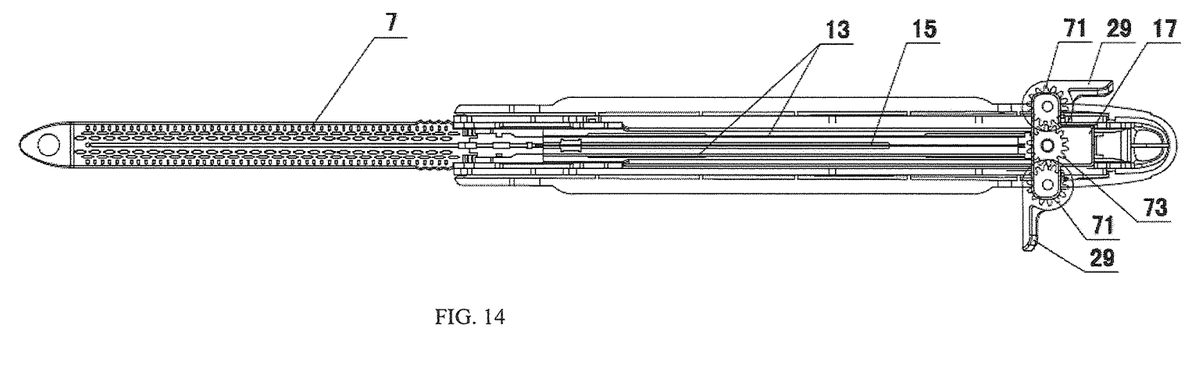
FIG. 14 is a cross-sectional view of an initial status of a linear surgical stapler in accordance with a fourth illustrated embodiment of the present application.
Figure 15:
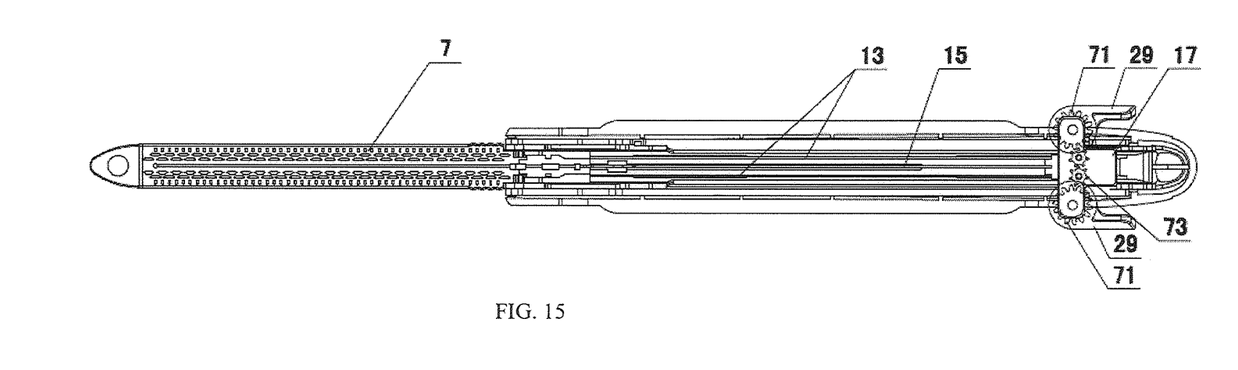
FIGS. 15 and 16 are cross-sectional views of an operating status of the linear surgical stapler in accordance with the fourth illustrated embodiment of the present application.
Figure 16:
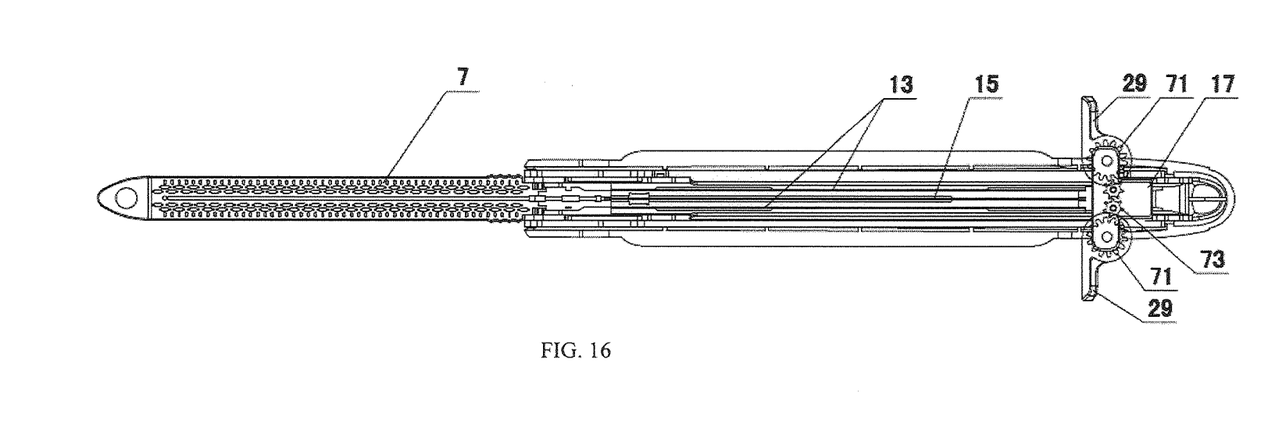

FIGS. 14, 15 and 16 disclose a linear surgical stapler in accordance with a fourth embodiment. Each operation button 29 is associated with a driving gear 71 which is rotatably mounted to the slider 17. The slider 17 includes at least one pinion gear 73 for meshing with the driving gear 71. Under this condition, the two operation buttons 29 are rotatable between two statuses where the operating surfaces of the operation buttons 29 are simultaneously perpendicular to the axis of the linear surgical stapler or simultaneously parallel to the axis of the linear surgical stapler. When the operating surfaces of the operation buttons 29 are simultaneously perpendicular to the axis of the linear surgical stapler, the operating portions 33 far from the pivot ends 31 protrude beyond the upper and lower jaws 1, 5 as shown in FIG. 15.

Certainly, the pinion gear 73 or the pinion gears 73 of the above fourth embodiment can be extended to even numbers, which can also achieve the similar functionality.

The joint portions (i.e., the pivot portions of the operation buttons 29 and the button base 21) of the operation buttons 29 may be of a piezoelectric material. That is to say, when the operation buttons 29 are connected to power, the operation buttons 29 can be converted from a status where the operating surface is parallel to the axis of the linear surgical stapler to another status where the operating surface is perpendicular to the axis of the linear surgical stapler. Since the piezoelectric material is already known, and thus detailed description thereof is omitted herein.

According to an embodiment, the description of both one end of the staple drive bar 13 and one end of the cutter pusher 15 are associated to a slider 17 not only includes that the one end of the staple drive bar 13 and the one end of the cutter pusher 15 are completely fixed to the slider 17, but also includes that the staple drive bar 13 and the cutter pusher 15 are fixed to the slider 17 along the axis of the linear surgical stapler. The reason is that in actual production, a certain amount of deformation of the upper and lower jaws 1, 5 during operation will cause that the staple drive bar 13 and the cutter pusher 15 generate a certain offset between the slider 17 along a direction perpendicular to the axis of the linear surgical stapler. Of course, the word "fixed" includes assembly errors.

The left side or the right side of the upper and lower jaws 1, 5 according to the present description refer to the left direction or the right direction of the upper and lower jaws 1, 5 when the surface of the cartridge 7 extends upwardly.

It should be noted that, those skilled in the art may make many improvements and modifications to the present application without departing from the principle of the present application, and these improvements and modifications also fall into the protection scope of the claims of the present application.

What is claimed is:

1. A linear surgical stapler comprising:
    upper and lower jaws capable of mutually being closed or opened with each other;
    an anvil and a cartridge respectively mounted on opposite far ends of the upper and lower jaws, a surface of the cartridge defining a plurality of slots arranged along an axis of the linear surgical stapler, each slot therein being provided with a staple pusher and a stapler engaging with the staple pusher, the lower jaw therein comprising a staple drive bar and a cutter pusher having a cutter on a far end of the cutter pusher, the staple drive bar and the cutter pusher being simultaneously movable along the axis of the linear surgical stapler, the staple drive bar being movable to sequentially drive the staple pusher; and
    a handle portion for closing the upper and lower jaws; wherein
    both one end of the staple drive bar and one end of the cutter pusher are associated to a slider;
    the slider is mounted with a button base which is fixed relative to the slider; and
    each lateral side of the button base is pivotally associated with an operation button which is rotatable between a first status where an operating surface of the operation button is perpendicular to the axis of the linear surgical stapler, and a second status where the operating surface of the operation button is parallel to the axis of the linear surgical stapler.

2. The linear surgical stapler as claimed in claim 1, comprising a first operation button pivotally associated with a first lateral side of the button base and a second operation button pivotally associated with a second lateral side of the button base, wherein the first and second operation buttons are symmetrical with each other and rotatable between the first status where the operating surfaces of the first and second operation buttons are simultaneously perpendicular to the axis of the linear surgical stapler, and the second status where the operating surfaces of the first and second operation buttons are simultaneously parallel to the axis of the linear surgical stapler.

3. The linear surgical stapler as claimed in claim 1, wherein the button base and the slider are either integral of one piece or separately made.

4. The linear surgical stapler as claimed in claim 1, wherein the button base defines a pivot hole playing a pivotal role and the pivot hole is located outside of the upper and lower jaws.

5. The linear surgical stapler as claimed in claim 1, wherein the button base comprises a main body fixed to the slider and a shoulder portion extending beyond the button base, the shoulder portion defining a pivot hole, the operation button comprising a pivot end and an operating portion, a pin being provided to extend through the pivot end and the pivot hole so that the operation button is pivotally mounted to the button base.

6. The linear surgical stapler as claimed in claim 5, wherein two lateral sides of the button base are associated with a pair of symmetrical shoulder portions each of which is pivotally mounted with the operation button.

7. The linear surgical stapler as claimed in claim 6, wherein a side surface of the button base comprises a plane surface and an arced surface smoothly connected with each other, the operation button comprising a front rotating-stop surface for mating with the plane surface and the arced surface.

8. The linear surgical stapler as claimed in claim 6, wherein the lower jaw comprises a pair of ribs formed on lateral sides thereof, and the operation button comprises a rear rotating-stop surface for mating with exterior surfaces of the ribs.

9. The linear surgical stapler as claimed in claim 6, wherein a top surface of the button base comprises a first recess and a second recess perpendicular to the first recess, and the operation button comprises a protrusion selectively mating with the first recess or the second recess.

10. A linear surgical stapler comprising:
    upper and lower jaws capable of mutually being closed or opened with each other;
    an anvil and a cartridge respectively mounted on opposite far ends of the upper and lower jaws, a surface of the cartridge defining a plurality of slots arranged along an axis of the linear surgical stapler, each slot therein being provided with a staple pusher and a stapler engaging with the staple pusher, the lower jaw therein comprising a staple drive bar and a cutter pusher having a cutter on a far end of the cutter pusher, the staple drive bar and the cutter pusher being simultaneously movable along the axis of the linear surgical stapler, the staple drive bar being movable to sequentially drive the staple pusher; and
    a handle portion for closing the upper and lower jaws; wherein
    both one end of the staple drive bar and one end of the cutter pusher are associated to a slider;
    the slider is mounted with a pair of operation buttons which are rotatable respect to the slider; and
    the operation buttons are rotatable between a first status where operating surfaces of the operation buttons are simultaneously perpendicular to the axis of the linear surgical stapler, and a second status where the operating surfaces of the operation buttons are simultaneously parallel to the axis of the linear surgical stapler, when the operating surfaces of the operation buttons are perpendicular to the axis of the linear surgical stapler, operating portions of the operation buttons located far from pivot ends protrude beyond the upper and lower jaws.

11. The linear surgical stapler as claimed in claim 10, wherein each operation button comprises a driving gear pivotally mounted to the slider, and the slider comprises even number of pinion gears for meshing with the driving gear.

12. The linear surgical stapler as claimed in claim 10, wherein pivot portions of the operation buttons and the button base are of a piezoelectric material.

13. A linear surgical stapler comprising:
    upper and lower jaws capable of mutually being closed or opened with each other;
    an anvil and a cartridge respectively mounted on opposite far ends of the upper and lower jaws, the cartridge comprising a plurality of staples;

a slider member slidable along a longitudinal axis of the linear surgical stapler for driving the staples to move towards the anvil, the slider member comprising a pair of shoulder portions; and a pair of operation buttons each of which is rotatably mounted to corresponding shoulder portion along a pivot axis, the pivot axis of the pair of operation buttons being parallel to each other; wherein the slider member is movable between an initial position and an operation position; and wherein when the slider member is located at the initial position, the operation buttons are rotatable about corresponding pivot axes; and when the slider member is located at the operation position, the operation buttons are not rotatable about the corresponding pivot axis.

14. The linear surgical stapler as claimed in claim 13, wherein the slider member comprises a button base with the pair of shoulder portions formed thereon, each side surface of the button base comprising a plane surface and an arced surface smoothly connected with the plane surface, each operation button comprising a front rotating-stop surface for mating with the plane surface and the arced surface when the slider member is located at the initial position.

15. The linear surgical stapler as claimed in claim 14, wherein the lower jaw comprises a pair of ribs formed on lateral sides thereof, and the operation button comprises a rear rotating-stop surface for mating with exterior surfaces of the ribs so as to prevent the operation buttons from rotating when the slider member is located at the operation position.

16. The linear surgical stapler as claimed in claim 14, wherein each shoulder portion comprises a first recess and a second recess perpendicular to the first recess, and each operation button comprises a protrusion selectively mating with the first recess or the second recess for positioning.

17. The linear surgical stapler as claimed in claim 14, wherein the pair of operation buttons are symmetrical with each other; and wherein when the slider member is located at the operation position, at least one of the operation buttons is perpendicular to the axis of the linear surgical stapler.

18. The linear surgical stapler as claimed in claim 17, wherein when the slider member is located at the operation position, both of the pair of operation buttons are perpendicular to the axis of the linear surgical stapler.

\* \* \* \* \*